US009359595B2

(12) United States Patent
Tark et al.

(10) Patent No.: US 9,359,595 B2
(45) Date of Patent: Jun. 7, 2016

(54) METHOD OF PREPARING CELLS SUSCEPTIBLE TO TRANSMISSIBLE SPONGIFORM ENCEPHALOPATHY AND THE CREATION OF TSE PERSISTENTLY INFECTED CELLS

(75) Inventors: Dong-Seob Tark, Gyeonggi-do (KR); Hyo-Jin Kim, Seoul (KR); Hyun-Joo Shon, Gyeonggi-do (KR); Yoon-Hee Lee, Gyeonggi-do (KR); Min-Jeong Kim, Seoul (KR); Eun-Im Yun, Gyeonggi-do (KR); In-Soo Cho, Gyeonggi-do (KR); Chang-Hee Kweon, Gyeonggi-do (KR); Yi-Seok Joo, Seoul (KR); Otto Windl, Addlestone Surrey (GB); Michael Neale, Addlestone Surrey (GB)

(73) Assignee: Animal, Plant and Fisheries Quarantine and Inspection Agency, Gyeonggi-do (KR)

( * ) Notice: Subject to any disclaimer, the term of this patent is extended or adjusted under 35 U.S.C. 154(b) by 226 days.

(21) Appl. No.: 13/512,010

(22) PCT Filed: Nov. 22, 2010

(86) PCT No.: PCT/KR2010/008260

§ 371 (c)(1), (2), (4) Date: May 24, 2012

(87) PCT Pub. No.: WO2011/065715

PCT Pub. Date: Jun. 3, 2011

(65) Prior Publication Data

US 2012/0237969 A1 Sep. 20, 2012

(30) Foreign Application Priority Data

Nov. 25, 2009 (KR) ........................ 10-2009-0114269

(51) Int. Cl.

*C12N 15/00* (2006.01)
*C12N 15/02* (2006.01)
*C12N 7/00* (2006.01)

(52) U.S. Cl.

CPC ........ *C12N 7/00* (2013.01); *C12N 2740/15043* (2013.01); *C12N 2790/10051* (2013.01)

(58) Field of Classification Search

None

See application file for complete search history.

(56) References Cited

PUBLICATIONS

Heinig et al, Protein Expression and Purification, 2010, 70:129-136.*
Cervenakova et al, PNAS, 1994, 91:12159-12162.*
Solassol et al, British Medical Bulletin, 2003, 66:87-97.*
Liu et al, J Biol Chem, 2002, 277:47671-47678.*
Vilette, Vet Res, 2008, 39-10:1-18.*
Bos taurus prp gene for prion protein, GenBank Accession No. AJ298878.1, Nov. 14, 2006.*
Courageot et al, Journal of General Virology, 2008, 89:341-347.*
Alais, S., et al., "Mouse Neuroblastoma Cells Release Prion Infectivity Associated with Exosomal Vesicles," *Biol. Cell.* 100:603-615, Ivry sur Seine France, England (Oct. 2008).
Bian, J., et al., "Cell-Based Quantification of Chronic Wasting Disease Prions," *J. Virol.* 84:8322-8326, American Society for Microbiology, United States (Jun. 2010).
Courageot, M.-P., et al., "A Cell Line Infectible by Prion Strains From Different Species," *J. Gen. Virol.* 89:341-347, Society for General Microbiology, England (Jan. 2008).
Crozet, C., et al., "Inhibition of $PrP^{Sc}$ formation by Lentiviral Gene Transfer of PrP Containing Dominant Negative Mutations," *J. Cell. Sci.* 117:5591-5597, Company of Biologists, England (2004).
Dull, T., et al., "A Third-Generation Lentivirus Vector with a Conditional Packaging System," *J. Virol.* 72:8463-8471, American Society for Microbiology, United States (1998).
Follenzi, A., et al., "Gene Transfer by Lentiviral Vectors is Limited by Nuclear Translocation and Rescued by HIV-1 *Pol* Sequences," *Nat. Genet.* 25:217-222, Nature Pub. Co., United States (2000).
Heinig, L., et al., "Inducible Expression of Chimpanzee Prion Protein (PrP) in Murine PrP Knock-Out Cells," *Protein Expr. Purif.* 70:129-136, Academic Press, United States (Sep. 2009).
Klöhn, P.-C., et al., "A Quantitative, Highly Sensitive Cell-Based Infectivity Assay For Mouse Scrapie Prions," *Proc. Natl. Acad. Sci. U.S.A.* 100:11666-11671, National Academy of Sciences, United States (2003).
Lawson, V.A., et al., "Mouse-Adapted Sporadic Human Creutzfeldt-Jakob Disease Prions Propagate in Cell Culture," *Int. J. Biochem. Cell Biol.* 40:2793-2801, Elsevier, Amsterdam (Jun. 2008).
Prusiner, S.B., "Scrapie Prions," *Annu. Rev. Microbiol.* 43:345-374, Annual Reviews, United States (1989).
Raymond, G.J., "Inhibition of Protease-Resistant Prion Protein Formation in a Transformed Deer Cell Line Infected with Chronic Wasting Disease," *J. Virol.* 80:596-604, American Society for Microbiology, United States (2006).
Solassol, J., et al., "Prion Propagation in Cultured Cells," *Br. Med. Bull.* 66:87-97, Oxford University Press, England (2003).
International Search Report and Written Opinion for International No. PCT/KR2010/008260, mailed on Aug. 18, 2011.

* cited by examiner

*Primary Examiner* — Valarie Bertoglio

(74) *Attorney, Agent, or Firm* — Sterne, Kessler, Goldstein & Fox, P.L.L.C.

(57) ABSTRACT

Disclosed is a method for preparation of transmissible spongiform encephalopathy (TSE) susceptible cells, and such cells may be efficiently used in diagnosis of TSE, etiology studies and development of novel therapeutics, etc.

2 Claims, 12 Drawing Sheets

Fig. 1

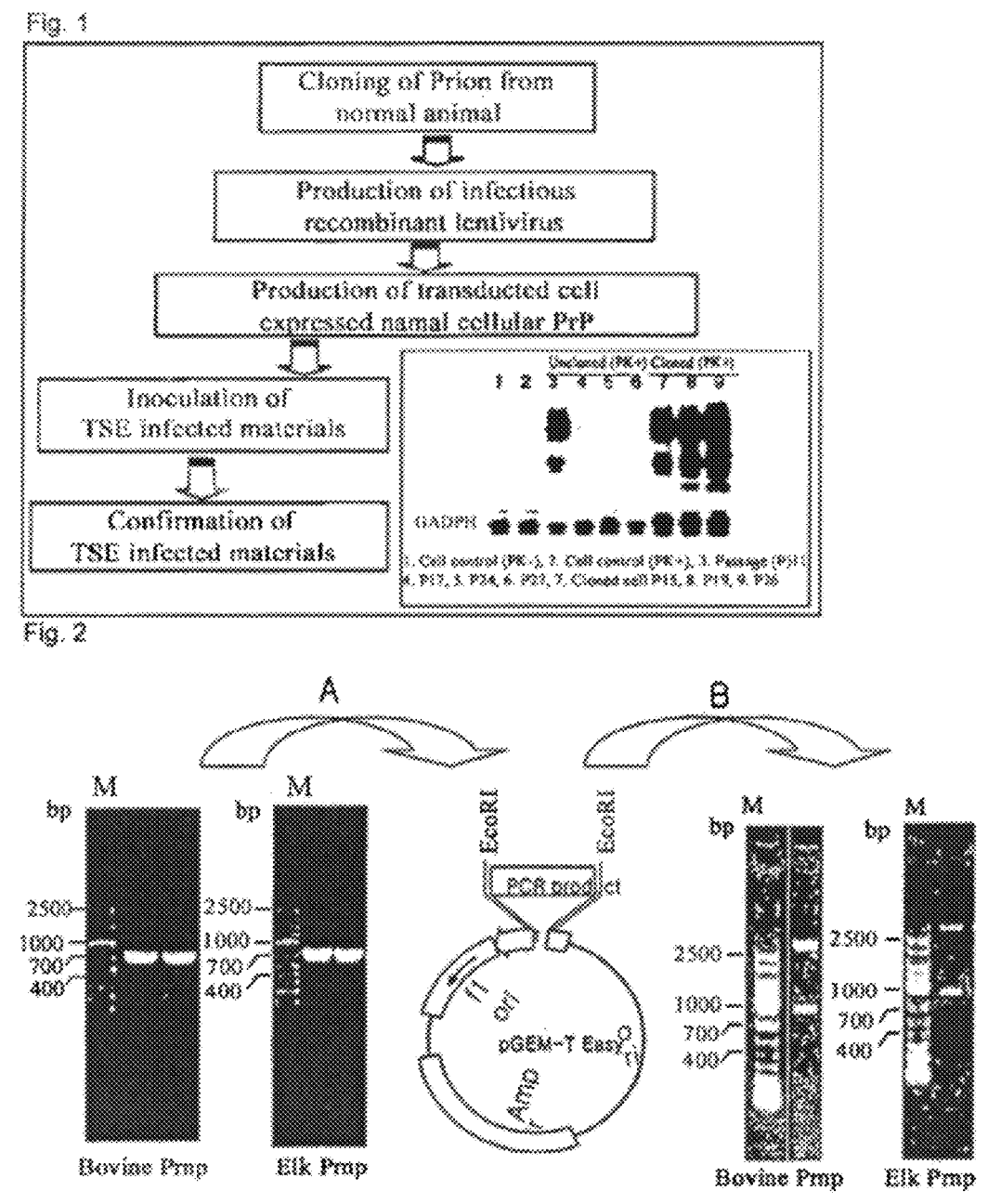

Cloning of Prion from normal animal

Production of infectious recombinant lentivirus

Production of transducted cell expressed namal cellular PrP

Inoculation of TSE infected materials

Confirmation of TSE infected materials

1. Cell control (PK-), 2. Cell control (PK+), 3. Passage (P)11, 4. P17, 5. P24, 6. P33, 7. Cloned cell P15, 8. P19, 9. P26

Fig. 2

Fig. 3 bovine-AJ298878
bovine Prnp-EU224471
PCR product

```
bovine-AJ298   65521  gtgatttttacatgggcatatgatgctgacaccctctttattttgcagataagtcatcatggtgaaaagccacataggcagttggatcctggttctctttgtggccatgtggagtgacgt
bovine Prnp-       1  ----------------------------------------------------------atggtgaaaagccacataggcagttggatcctggttctctttgtggccatgtggagtgacgt
080403-13_M0      58  ----------------------------------------------------------atggtgaaaagccacataggcagttggatcctggttctctttgtggccatgtggagtgacgt
080403-13_00     874  ----------------------------------------------------------atggtgaaaagccacataggcagttggatcctggttctctttgtggccatgtggagtgacgt

bovine-AJ298   65641  gggcctctgcaagaagcgaccaaaacctggaggaggatggaacactgggggagccgatacccaggacagggcagtcctggaggcaaccgttatccacctcagggagggggtggctgggg
bovine Prnp-      63  gggcctctgcaagaagcgaccaaaacctggaggaggatggaacactgggggagccgatacccaggacagggcagtcctggaggcaaccgttatccacctcagggagggggtggctgggg
080403-13_M0     120  gggcctctgcaagaagcgaccaaaacctggaggaggatggaacactgggggagccgatacccaggacagggcagtcctggaggcaaccgttatccacctcagggagggggtggctgggg
080403-13_00     812  gggcctctgcaagaagcgaccaaaacctggaggaggatggaacactgggggagccgatacccaggacagggcagtcctggaggcaaccgttatccacctcagggagggggtggctgggg

bovine-AJ298   65761  tcagccccatggaggtggctggggccagcctcatggaggtggctggggccagcctcatggaggtggctggggtcagccccatggtggtggctggggacagccacatggtggtggaggctg
bovine Prnp-     183  tcagccccatggaggtggctggggccagcctcatggaggtggctggggccagcctcatggaggtggctggggtcagccccatggtggtggctggggacagccacatggtggtggaggctg
080403-13_M0     240  tcagccccatggaggtggctggggccagcctcatggaggtggctggggccagcctcatggaggtggctggggtcagccccatggtggtggctggggacagccacatggtggtggaggctg
080403-13_00     692  tcagccccatggaggtggctggggccagcctcatggaggtggctggggccagcctcatggaggtggctggggtcagccccatggtggtggctggggacagccacatggtggtggaggctg

bovine-AJ298   65881  gggtcaaggtggtacccacggtcaatggaacaaacccagtaagccaaaaaccaacatgaagcatgtggcaggagctgctgcagctggagcagtggtagggggccttggtggctacatgct
bovine Prnp-     303  gggtcaaggtggtacccacggtcaatggaacaaacccagtaagccaaaaaccaacatgaagcatgtggcaggagctgctgcagctggagcagtggtagggggccttggtggctacatgct
080403-13_M0     360  gggtcaaggtggtacccacggtcaatggaacaaacccagtaagccaaaaaccaacatgaagcatgtggcaggagctgctgcagctggagcagtggtagggggccttggtggctacatgct
080403-13_00     572  gggtcaaggtggtacccacggtcaatggaacaaacccagtaagccaaaaaccaacatgaagcatgtggcaggagctgctgcagctggagcagtggtagggggccttggtggctacatgct

bovine-AJ298   66001  gggaagtgccatgagcaggcctgttatacattttggcagtgactatgaggaccgttactatcgtgaaaacatgcaccgttaccccaaccaagtgtactacaggccagtggatcagtatag
bovine Prnp-     423  gggaagtgccatgagcaggcctgttatacattttggcagtgactatgaggaccgttactatcgtgaaaacatgcaccgttaccccaaccaagtgtactacaggccagtggatcagtatag
080403-13_M0     480  gggaagtgccatgagcaggcctgttatacattttggcagtgactatgaggaccgttactatcgtgaaaacatgcaccgttaccccaaccaagtgtactacaggccagtggatcagtatag
080403-13_00     452  gggaagtgccatgagcaggcctgttatacattttggcagtgactatgaggaccgttactatcgtgaaaacatgcaccgttaccccaaccaagtgtactacaggccagtggatcagtatag

bovine-AJ298   66121  taaccagaacaactttgtgcatgactgtgtcaacatcacagtcaaggaacacacagtcaccaccaccaccaagggggagaacttcaccgaaactgacatcaagatgatggagcgagtggt
bovine Prnp-     543  taaccagaacaactttgtgcatgactgtgtcaacatcacagtcaaggaacacacagtcaccaccaccaccaagggggagaacttcaccgaaactgacatcaagatgatggagcgagtggt
080403-13_M0     600  taaccagaacaactttgtgcatgactgtgtcaacatcacagtcaaggaacacacagtcaccaccaccaccaagggggagaacttcaccgaaactgacatcaagatgatggagcgagtggt
080403-13_00     332  taaccagaacaactttgtgcatgactgtgtcaacatcacagtcaaggaacacacagtcaccaccaccaccaagggggagaacttcaccgaaactgacatcaagatgatggagcgagtggt

bovine-AJ298   66241  ggagcaaatgtgcattacccagtaccagagagaatcccaggcttattaccaacgaggggcaagtgtgatcctcttctcttcccctcctgtgatcctcctcatctctttcctcatttttct
bovine Prnp-     663  ggagcaaatgtgcattacccagtaccagagagaatcccaggcttattaccaacgaggggcaagtgtgatcctcttctcttcccctcctgtgatcctcctcatctctttcctcatttttct
080403-13_M0     720  ggagcaaatgtgcattacccagtaccagagagaatcccaggcttattaccaacgaggggcaagtgtgatcctcttctcttcccctcctgtgatcctcctcatctctttcctcatttttct
080403-13_00     212  ggagcaaatgtgcattacccagtaccagagagaatcccaggcttattaccaacgaggggcaagtgtgatcctcttctcttcccctcctgtgatcctcctcatctctttcctcatttttct

bovine-AJ298   66361  catagtaggataggggcaaccttcctgttttcattatcttcttaatctttaccaggttgggggagggagtatctacctgcagccccgtagtggtggtgtctcatttcttgcttctctctt
bovine Prnp-     783  catagtaggatag-----------------------------------------------------------------------------------------------------------
080403-13_M0     840  catagtaggatag-----------------------------------------------------------------------------------------------------------
080403-13_00      92  catagtaggatag-----------------------------------------------------------------------------------------------------------
```

Fig. 4

```
American elk-EU082291  american elk     1  ------------------------------------------------------------------------------atggtgaaacgccacataggcagctggatcctag
Elk Prnp          ┌─  080403-13_E0   857  tcactagtgattagcggccgcgccacc---------------------------------------------------atggtgaaacgccacataggcagctggatcctag
(PCR Product)     └─  080403-13_G0     1  nnnnnccaatatcacgcgttggggctctccatatggtcgacctgcaggcggccgcgaattcactagtgattagcggccgcgccaccatggtgaaacgccacataggcagctggatcctag

                       american elk    35  ttctctttgtggccatgtggagtgacgtcggcctctgcaagaagcgaccaaaacctggaggaggatggaacactgggggagccgatacccgggacagggaagtcctggaggcaaccgct
                       080403-13_E0   796  ttctctttgtggccatgtggagtgacgtcggcctctgcaagaagcgaccaaaacctggaggaggatggaacactgggggagccgatacccgggacagggaagtcctggaggcaaccgct
                       080403-13_G0   121  ttctctttgtggccatgtggagtgacgtcggcctctgcaagaagcgaccaaaacctggaggaggatggaacactgggggagccgatacccgggacagggaagtcctggaggcaaccgct

                       american elk   155  atccacctcagggagggggtggctggggtcagccccatggaggtggctggggccaacctcatggaggtggctggggtcagccccatggtggtggctggggacagccacatggtggtggag
                       080403-13_E0   676  atccacctcagggagggggtggctggggtcagccccatggaggtggctggggccaacctcatggaggtggctggggtcagccccatggtggtggctggggacagccacatggtggtggag
                       080403-13_G0   241  atccacctcagggagggggtggctggggtcagccccatggaggtggctggggccaacctcatggaggtggctggggtcagccccatggtggtggctggggacagccacatggtggtggag

                       american elk   275  gctggggtcaaggtggtacccacagtcagtggaacaagcccagtaaaccaaaaaccaacatgaagcatgtggcaggagctgctgcagctggagcagtggtaggggggcctcggtggctaca
                       080403-13_E0   556  gctggggtcaaggtggtacccacagtcagtggaacaagcccagtaaaccaaaaaccaacatgaagcatgtggcaggagctgctgcagctggagcagtggtaggggggcctcggtggctaca
                       080403-13_G0   361  gctggggtcaaggtggtacccacagtcagtggaacaagcccagtaaaccaaaaaccaacatgaagcatgtggcaggagctgctgcagctggagcagtggtaggggggcctcggtggctaca

                       american elk   395  tgctgggaagtgccatgagcaggcctcttatacattttggcaatgactatgaggaccgttactatcgtgaaaacatgtaccgttaccccaaccaagtgtactacaggccagtggatcagt
                       080403-13_E0   436  tgctgggaagtgccatgagcaggcctcttatacattttggcaatgactatgaggaccgttactatcgtgaaaacatgtaccgttaccccaaccaagtgtactacaggccagtggatcagt
                       080403-13_G0   481  tgctgggaagtgccatgagcaggcctcttatacattttggcaatgactatgaggaccgttactatcgtgaaaacatgtaccgttaccccaaccaagtgtactacaggccagtggatcagt

                       american elk   515  ataataaccagaacacctttgtgcatgactgtgtcaacatcacagtcaagcaacacacagtcaccaccaccaccaaggggggagaacttcaccgaaactgacatcaagatgatggagcgag
                       080403-13_E0   316  ataataaccagaacacctttgtgcatgactgtgtcaacatcacagtcaagcaacacacagtcaccaccaccaccaaggggggagaacttcaccgaaactgacatcaagatgatggagcgag
                       080403-13_G0   601  ataataaccagaacacctttgtgcatgactgtgtcaacatcacagtcaagcaacacacagtcaccaccaccaccaaggggggagaacttcaccgaaactgacatcaagatgatggagcgag

                       american elk   635  ttgtggagcaaatgtgcatcacccagtaccagagagaatccgaggcttattaccaaagaggggcaagtgtgatcctcttctcctcccctcctgtgatcctcctcatctctttcctcattt
                       080403-13_E0   196  ttgtggagcaaatgtgcatcacccagtaccagagagaatccgaggcttattaccaaagaggggcaagtgtgatcctcttctcctcccctcctgtgatcctcctcatctctttcctcattt
                       080403-13_G0   721  ttgtggagcaaatgtgcatcacccagtaccagagagaatccgaggcttattaccaaagaggggcaagtgtgatcctcttctcctcccctcctgtgatcctcctcatctctttcctcattt

                       american elk   755  ttctcatagtaggatag--------------------------------------------------
                       080403-13_E0    76  ttctcatagtaggatagctcgagccgaatcgaattcccgcggccgccatgcggccggagctggttggcctcccnnn
                       080403-13_G0   841  ttctcatagtaggatag--------------------------------------------------
```

Fig. 9
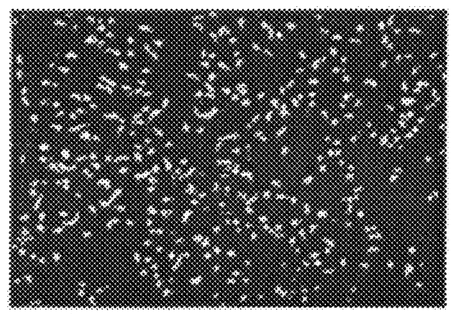
MDBK Control cell (non-expressive cell)
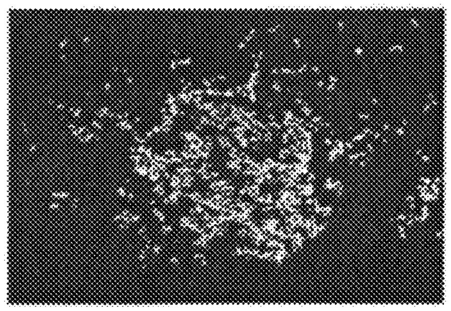
Transduced cell (MDBK C1-2F)
Fig. 10
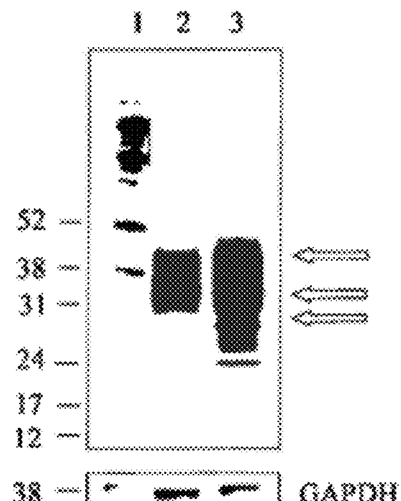
1: Molecular marker
2: MDBK
3: MDBK C1-2F

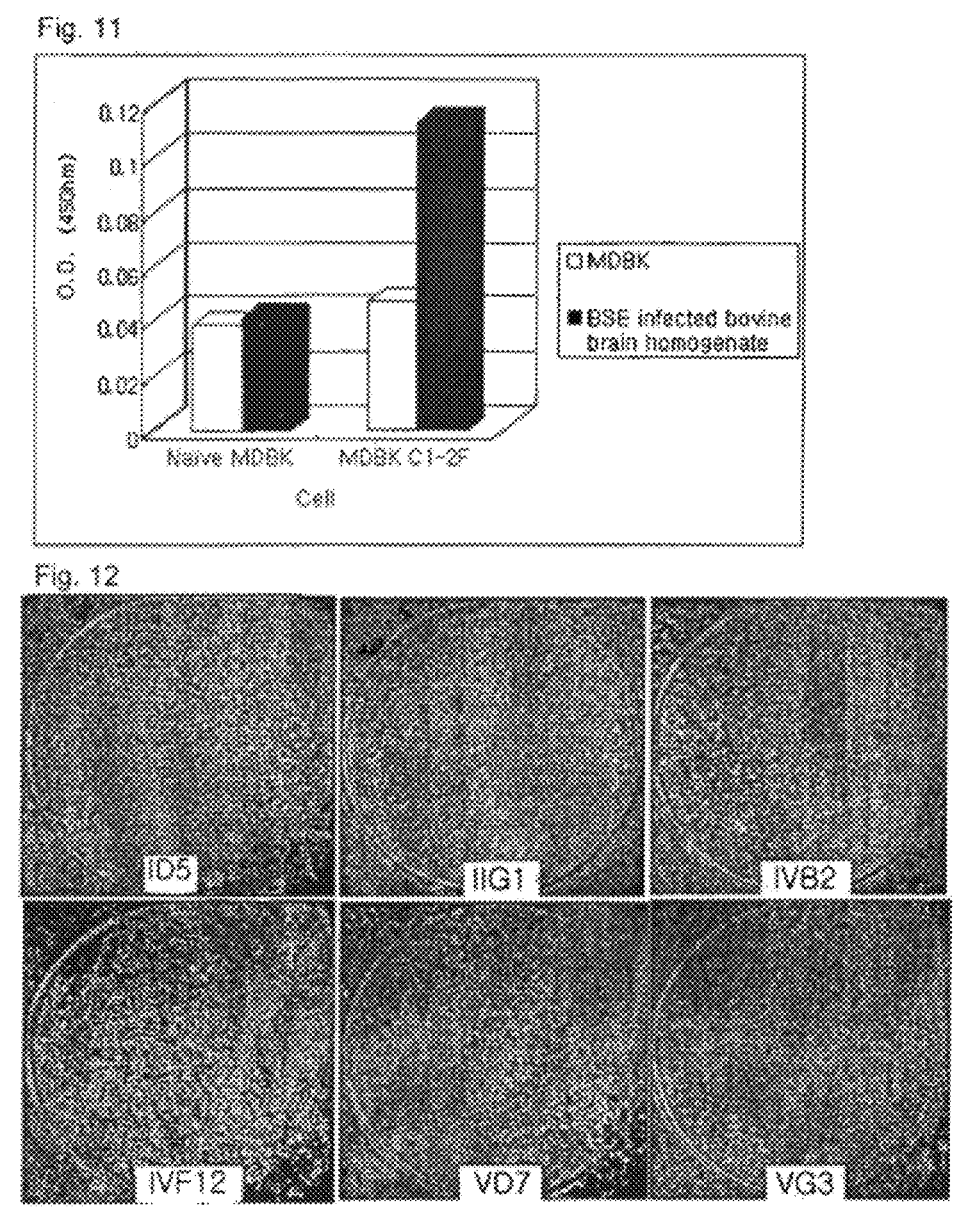

Naive MDBK
MDBK C1-2F

Cell

□ MDBK
■ BSE infected bovine brain homogenate

Fig. 12

ID5
IIG1
IVB2
IVF12
VD7
VG3

1. Cell control (PK−), 2. Cell control (PK+), 3. Passage (P) 11
4. P17, 5. P24, 6. P27, 7. Cloned cell P15, 8. P19, 9. P26

1. Molecular marker
2. R5C-1 (passage 17) - PK(10ug/ml) non-treated
3. R5C-1 (passage 17) - PK(10ug/ml) treated
4. R5C-2 (passage 17) - PK(10ug/ml) non-treated
5. R5C-2 (passage 17) - PK(10ug/ml) treated

METHOD OF PREPARING CELLS SUSCEPTIBLE TO TRANSMISSIBLE SPONGIFORM ENCEPHALOPATHY AND THE CREATION OF TSE PERSISTENTLY INFECTED CELLS

TECHNICAL FIELD

This application claims priority from Korean Patent Application No. 10-2009-0114269, filed on Nov. 25, 2009 in the Korean intellectual Property Office, the entire disclosure of which is incorporated herein by reference.

The present invention relates to a method for preparation of a cell line susceptible to transmissible spongiform encephalopathy (TSE) and use of the cells prepared by the same.

BACKGROUND ART

Transmissible spongiform encephalopathy (TSE) is known as a neuro-degenerative disorder causing serious degeneration of neurons and includes, for example, bovine spongiform encephalopathy (BSE), scrapie, Creutzfeldt-Jakob disease (CJD), Gerstmann-Straussler-Scheinker syndrome, Kuru, transmissible mink encephalopathy, chronic wasting disease, feline spongiform encephalopathy, etc. which often affect humans and animals. In the case of BSE, the linkage to vCJD which is a human form of BSE has been reported.

The causative agent of TSE does not have immunogenicity while having relatively long incubation period. From a histopathological examination of BSE affected bovine brain tissue, it was demonstrated that disease-related spongiosis was generated due to damage of nerve cells and deposition of abnormal protein fibers.

A causative agent of TSE is an infectious protein called an abnormal prion. Contrary to typical viruses requiring nucleic acid, the abnormal prion contains no nucleic acid but consists of protein alone. Regarding TSE, it has been reported that, when an abnormal prion ($PrP^{sc}$) as an infectious agent is combined with a normal prion ($PrP^{c}$), the combined material is transformed into a pathogenic prion, in turn being accumulated in brain tissue (Prusiner 1989). A serious problem is that a tissue infected with such a pathogenic prion, that is, $PrP^{sc}$ may also infect cells and, when inoculating an animal with the infected cells, a prion disease may be derived. Accordingly, we believe that, if a specific cell susceptible to the prion disease is developed, this cell may be advantageous for a variety of studies, for example, screening of anti-prion substances, formation and inhibition of pathogenic prions, a biological marker for diagnosis of the prion disease, and the like.

DISCLOSURE OF INVENTION

Technical Problem

However, development and/or selection of cells having susceptibility for TSE, which are necessary for the foregoing studies, is still restricted. Currently developed cells generally comprise mouse-derived cells (Solassol et al., 2003) and, other than the mouse-derived cells, confirmation of abnormal prion infection of pure cells of the mouse has been conducted by over-expression of normal prions contained in a mouse, a sheep, etc. using RK-13 cells (Courageot, 2008, Victoria, 2008). However, cell cultures susceptible to BSE from cattle or CJD from humans has never been developed. In addition, further research and investigation into a chronic wasting disease (CWD) except for cells provided by Raymond et al. (2006), still need to be conducted. Raymond et al. (2006) and Telling et al (2010) reported the establishment of CWD susceptible cell lines, but no further follow up was been done. So, further research and investigation into a CWD still need to be conducted.

Accordingly, there is now a strong requirement for developing a novel cell line susceptible to transmissible spongiform encephalopathies, being advantageous for diagnosis of BSE, scrapie, vCJD and other related prion diseases.

Solution to Problem

In order to resolve the problems described above, an object of the present invention is to provide a method for preparation of a cell line having susceptibility to infection by the etiologic agent of transmissible spongiform encephalopathy (TSE).

A second object of the present invention is to provide a cell susceptible to TSE infection, which is useful for diagnosis of TSE.

A third object of the present invention is to provide a method for preparation of TSE infected cells using the foregoing TSE-susceptible cell.

A fourth object of the present invention is to provide TSE infected cells which are applicable to various studies including, for example, selection of therapeutic materials for TSE, identification of etiology, etc.

Advantageous Effects of Invention

According to one aspect of the present invention in order to accomplish the foregoing purposes, there is provided a method for preparation of a cell susceptible to transmissible spongiform encephalopathy (TSE), which includes: separating a normal prion protein (PRNP) gene from a brain of a major natural host of TSE and cloning the same; inserting the cloned PRNP gene into a lentivirus transfer vector to produce an infectious recombinant lentivirus; and inoculating the infectious recombinant lentivirus into a non-human mammalian cell-line to produce transduced cells expressing a normal cellular prion protein.

According to another aspect of the present invention, there is provided a method for preparation of TSE infected cells, which includes; extracting the DNA for the PRNP gene from the brain of susceptible animals to TSE and cloning the same; inserting the cloned PRNP gene into a lentivirus transfer vector to produce an infectious recombinant lentivirus; inoculating the infectious recombinant lentivirus into a mammalian cell-line to produce the transduced cell expressing a normal celluar prion protein; selecting one of multiple transduced cells, which expresses the normal cellular prion protein; inoculating a TSE infected brain tissue into the selected transduced cell expressing a normal cellular prion protein in order to screen infected cells; and cloning the TSE infected cells to confirm the TSE infected cell-line.

Therefore, the present invention may enable ex vivo cell cultivation of various etiologic agents of TSE, such as BSE, CWD, Scrapie and CJD, in the laboratory. TSE susceptible cells prepared according to the present invention which are infectious or infected may be advantageously used in a wide range of applications including, for example, TSE diagnosis, etiological identification, development of novel therapeutics, and so forth.

BRIEF DESCRIPTION OF DRAWINGS

The above and other objects, features an d other advantages of the present invention will be more clearly understood from the following detailed description taken in conjunction with the accompanying drawings, in which:

FIG. 1 is a flow diagram illustrating a process of preparing TSE susceptible cells and TSE infected cell according to one embodiment of the present invention;

FIG. 2 illustrates a process of cloning each of complete bovine PRNP gene and elk PRNP gene, respectively, and confirming the same;

FIG. 3 shows a complete genomic sequence of the bovine PRNP gene (SEQ ID NO:1) used in the present invention;

FIG. 4 shows a complete genomic sequence of the elk PRNP gene (SEQ ID NO:2) used in the present invention;

FIG. 6 illustrates the production and determination of recombinant virus; The GFP expression of transduced cell was observed under fluorescent microscope. The titer was about $10^6$ to $10^7$ transduction unit (TU). HIV-1 p24 expression level was confirmed by western blotting (WB).

FIG. 9 shows expression of recombinant prion protein determined by fluorescent antibody assay (FA) of transduced MDBK cells;

FIG. 10 shows expression of recombinant prion protein determined by western blotting of transduced MDBK cells;

FIG. 11 is a graph illustrating results of ELISA that demonstrate BSE ($PrP^{BSE}$) infection of transduced MMDBK cells;

FIG. 12 illustrates SSCA results to demonstrate $PrP^{BSE}$ infection of transduced MDBK cells;

BEST MODE FOR CARRYING OUT THE INVENTION

Figure 5:
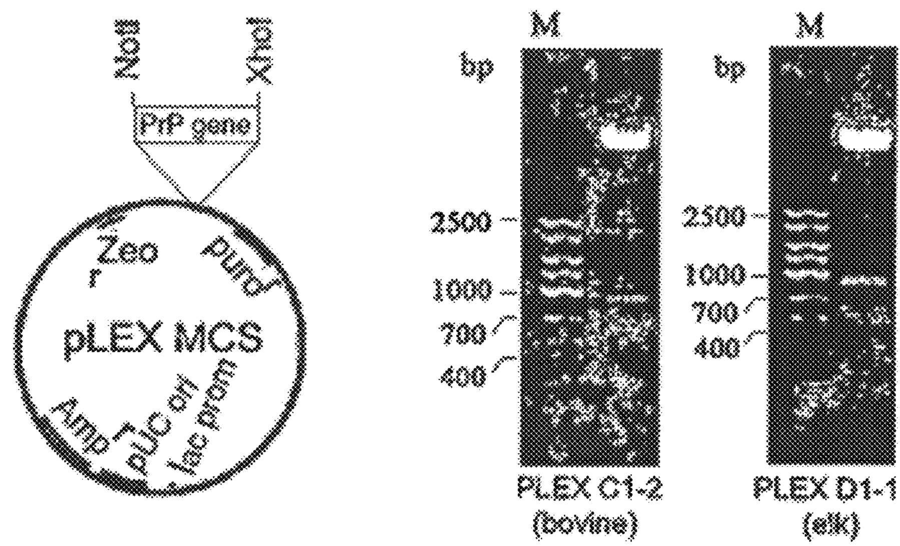
FIG. 5 illustrates results of cloning bovine PRNP and elk PRNP in the pLEX Multiple Cloning Site transfer vectors, respectively.

Hereinafter, preferred embodiments of the present invention will be described in more detail through the following examples, in conjunction with accompanying drawings.

According to an exemplary embodiment of the present invention, a cell susceptible to TSE infection may be prepared by cloning a complete normal PRNP gene of an animal susceptible to TSE (such as cattle, elk, etc.) and producing infectious lentivirus having a gene (PRNP), which encodes cellular prion protein ($PrP^C$), via a lentivirus expression system; and infecting commercially available mammalian cells such as MDBK, Vero, N2a, RK-13, etc., with the lentivirus to produce transduced cells continuously expressing bovine or elk prion proteins. Using a cell culture broth containing phorbol 12-myristate 13-acetate (PMA) as well as the transduced cells produced as described above, BSE or CWD infectious or infected cells may be prepared.

With regard to preparation of TSE susceptible cells according to the inventive method, the PRNP gene is firstly extracted from the brain cells of a natural TSE host such as cattle or elk and is cloned into a transfer vector. For production of such PRNP gene from the brain of the major natural host, gene amplification may be conducted using a specific primer set. In order to conduct cloning of an amplified gene into a specific transfer vector and determine whether the normal PRNP gene was correctly cloned, gene sequencing may be performed.

By inserting the transfer vector having the normal PRNP gene correctly cloned therein into lentivirus, infectious recombinant lentivirus is prepared. Production of recombinant lentivirus has been reported (see Follensi et al., 2000, Nat. Genet. 25, 217-222, Dul et al., (1998) Virol. 72, 8463-8471). According to conventional techniques known in related studies, transduced cells may be selected. For instance, in order to select transduced cells from non-transduced cells, resistance to a particular antibiotic (for example, puromycin) may be utilized, the transduced cells being resistance to this antibiotic.

The infectious recombinant lentivirus is then inoculated into a mammalian cell-line to produce the transduced cell expressing $PrP^C$. Expression of bovine or elk prion protein in the transduced cells may be detected using a fluorescent antibody assay (FA).

Such cells which are TSE susceptible may be used in various applications including, for example but not limited to, the diagnosis of different TSEs and/or etiology studies thereof.

The present invention may provide ex vivo replication and/or amplification of infectious prions on the basis of a lentivirus expression system and an incubation system including the addition of PMA to a cell culture medium. Such a system has advantages of enabling selection and provision of cells susceptible to TSE, especially, BSE and CWD. Therefore, proliferation or amplification of abnormal prion protein in cell culture means that infection or invasion of $PrP^{Sc}$ to cultured cell is established, the infected cell is proliferated and such infected cells are persistently infected even following several sub-cultures.

In order to accomplish the foregoing purposes, the present invention describes production of a transduced cell-line expressing prion protein by inoculating normal mammalian cell-lines such as MDBK, Vero, RK-13, N2a cell, etc with infectious recombinant lentivirus, which contain PRNP of elk and/or cattle. The cell-line produced is then inoculated with BSE or CWD infected brain tissue and incubation thereof is executed by adding PMA to the cell culture medium.

A method for preparation of TSE infected cells according to the present invention may include the following processes:

Firstly, the normal prion protein gene (PRNP) is extracted from the brain cells of the major natural hosts of TSE such as cattle or elk, followed by cloning the same into a transfer vector. The cloned PRNP gene is then inserted into a lentivirus transfer vector to produce infectious recombinant lentivirus. Following this, after inoculating the infectious recombinant lentivirus into a mammalian cell-line to form transduced cells expressing $PrP^C$, specifically cells expressing $PrP^C$ were selected from these transducated cells. The selected cells are then inoculated with TSE infected brain tissue and incubated in a culture medium containing PMA. Following screening and cloning infected cells, a TSE infected cell-line is established.

The mammalian cell-line is not particularly restricted but may include, for example, MDBK, Vero, RK-13, N2a, and the like.

When inoculating the transduced cell selected above with TSE infected brain tissue and incubating the same, a culture medium may contain PMA. For instance, a DMEM cell culture broth (PMA, that is, phorbol 12-myristate 13-acetate; fetal bovine serum; penicillin; streptomycin; non-essential amino acid, etc.) may be used for incubation of cells.

Infection or proliferation of infectious prions in cells may be determined or assessed by the standard scrapie cell assay (SSCA) (see Klohn, P. C., Stoltze. L., Flechsig. E., Enari. M. & Weissmann, C. A. Quantitative, highly sensitive cell-based infectivity assay for mouse scrapie prions, *Proc. Nat.l Acad Sci. USA* 2003. 100, 11666-11671), Enzyme Linked Immuno-Sorbent Assay (ELISA) and Western blotting (WB).

TSE infected cells obtained according to the inventive method may be utilized in screening of anti-prion substances, formation of abnormal prion and inhibition thereof, development of a biological marker for TSE diagnosis, etc.

The following examples will be given of illustrating preferred embodiments of the present invention. However, such embodiments are provided for illustrative purposes but are not construed to restrict the scope of the present invention as defined by the appended claims.

EXAMPLE 1

Yield of Normal Prion Protein Genes (PRNPs) from Cattle and/or Elk, Analysis of Genetic Sequence Thereof In order to obtain bovine and elk PRNPs, primer sets listed in TABLE 1 enabling amplification of the whole gene were synthesized. Primer sequence was designed using the bovine gene (GenBank: AJ298878) and, for gene cloning, NotI and XhoI restriction enzyme sites were added to a forward primer and a reverse primer, respectively. Using the foregoing primer set, whole PRNP genes from brain tissues of cattle (Korean native cattle; Hanwoo) and elk were amplified under PCR conditions in TABLE 1. As shown in FIG. 2A, amplification of bovine and elk PRNP genes were produced and such amplified genes were inserted into the pGEM-T Easy Vector (Promega) then treated using EcoRI as a restriction enzyme site exists in the plasmid. As a result, it was found that a target gene is inserted in the plasmid (FIG. 2B) and, in order to determine whether bovine and elk PRNPs were cloned in the plasmid, DNA sequencing of the target gene was performed. DNA sequencing of the apparent bovine and elk genes were compared with genes with Accession Numbers AJ298878, EU224471 (cattle) and EU082291 (American elk) registered in GenBank. From results of the sequencing, cloning of the target genes was demonstrated (FIGS. 3 and 4).

As overall results of the foregoing review, FIG. 2 illustrates a process of cloning and confirming each of complete bovine and elk prion protein genes. More particular, FIG. 2A exhibits PRNP PCR products of cattle and elk, while FIG. 2B shows results of a process that inserts each PRNP PCR product into the pGEM-T Easy vector, treats the same with a restriction enzyme in the plasmid and conducts electrophoresis thereof using a 1% (w/v) agarose gel. FIG. 3 shows complete bovine PRNP gene sequence(SEQ ID NO: 1) and results of EU224471). Likewise, FIG. 4 shows complete elk PRNP gene sequence(SEQ ID NO: 2) and results of comparing this sequence with genes registered in GenBank (EU082291).

TABLE 1

Table 1

| Primer | Sequence | PCR condition | |
|---|---|---|---|
| Forward primer (nBoPrP-F) (SEQ ID NO: 3) | 5'-AGCGGCCGCGCCA CCATGGTGAAAAGCCA CATAGG-3' | 94° C. 5 min<br>94° C. 30 sec<br>60° C. 30 sec<br>72° C. 1 min 30 sec | 1 cycle<br>30 cycle |
| Reverse primer (xBoPrP-R) (SEQ ID NO: 4) | 5'-CGGCTCGAGCTAT CCTACTATGAGAAAAA TGA-3' | 72° C. 15 min<br>4° C. ∞ | 1 cycle<br>1 cycle |

Primer Set and PCR Amplification Condition

EXAMPLE 2

Production and Determination of Recombinant Lentivirus

Figure 6:
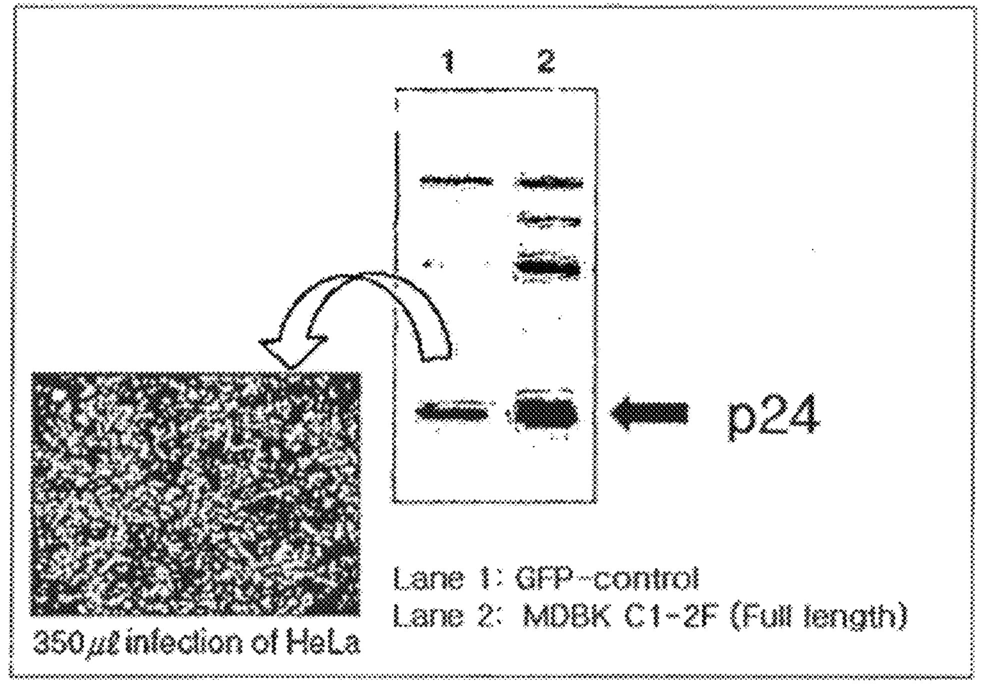
FIG. 6 illustrates results of infectious lentivirus confirmation as well as titer measurement.

First, as shown in FIG. 5, the PRNP gene containing cloned sequence was inserted into the pLEX MCS transfer vector (Open Biosystem) using specific restriction enzymes NotI and XhoI, followed by cloning the same. Then, in order to determine whether the insertion of the clone into the transfer vector was successfully conducted, agarose gel electrophoresis was performed after treatment of PRNP using the same enzymes NotI and XhoI. Such cloned transfer vector was mixed with an envelop glycoprotein expression vector and a packaging vector in a relative molar ratio of 1:1:1, followed by transfection of the same into 293T cells using lipofectamine Plus (Invitrogen, USA). Forty eight hours after transfection, a cell culture supernatant containing recombinant virus was recovered, filtered using a membrane filter with a pore size of 0.45 μm (Nalgene, USA), and stored immediately at −70° C. A titer value of the recombinant virus was measured in HeLa cells. Under fluorescent microscopy, GFP expression was observed in transduced cells. The measured titer value was about $10^6$ to $10^7$ transduction unit (TU) (FIG. 6).

For indirect determination of expression in the recombinant virus infected cells, HIV-1 p24 expression levels were determined by western blotting (WB). Briefly, the present experiment was performed by: adding 30 μl of virus culture supernatant to 5 times volume of sample buffer to dissolve cells therein; conducting electrophoresis of the same using 12% SDS polyacrylamide gel; carrying the fractioned viral protein obtained by electrophoresis into a membrane; and reacting the same with primary anti-p24 monoclonal antibody (dilution ratio 1:1,000) at room temperature for 5 hours. An immune complex reaction was visualized using CDP star and subjected to image analysis using the LAS-4000 system (Fuji, Japan) to measure chemiluminescence. Results of the analysis are shown in FIG. 6.

EXAMPLE 3

Recombinant Lentiviral Cell Infection and Selection of Transduced Cell

Figure 7:
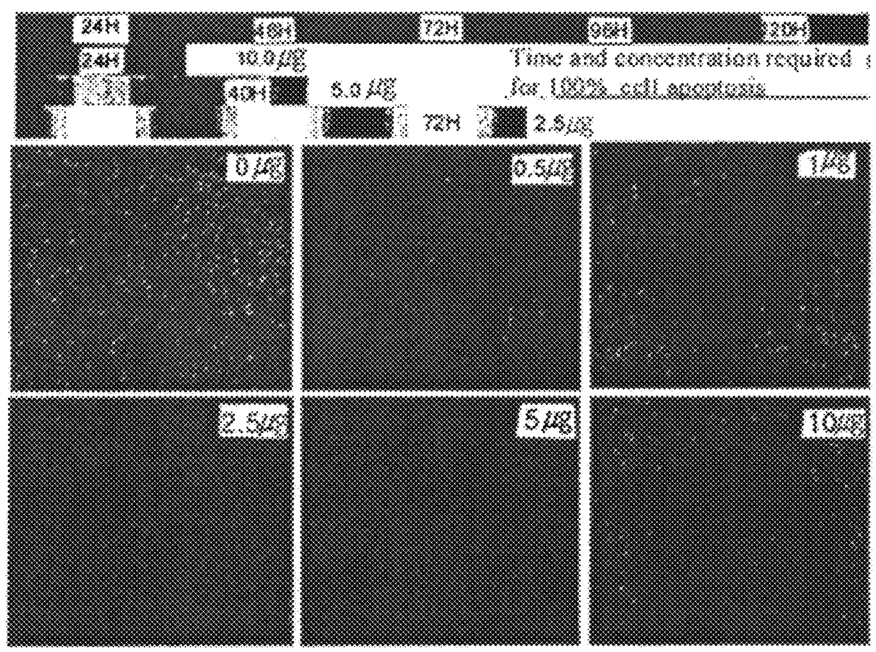
FIG. 7 illustrates a process of determining a proper concentration of puromycin for selection of transduced MDBK cells.

For production of transduced cells using recombinant lentivirus and selection thereof, Puromycin was used. According to MDBK or other mammalian cells, 0 to 10 μg/ml of puromycin was added to the cells, followed by determination of an optimal concentration at which cell death (or apoptosis) is observed within 3 to 4 days (FIG. 7). Finally, the optimal concentration of puromycin was predetermined in the range of 1.5 to 2.5 μg/ml and used for selecting the transduced cells.

Figure 8:
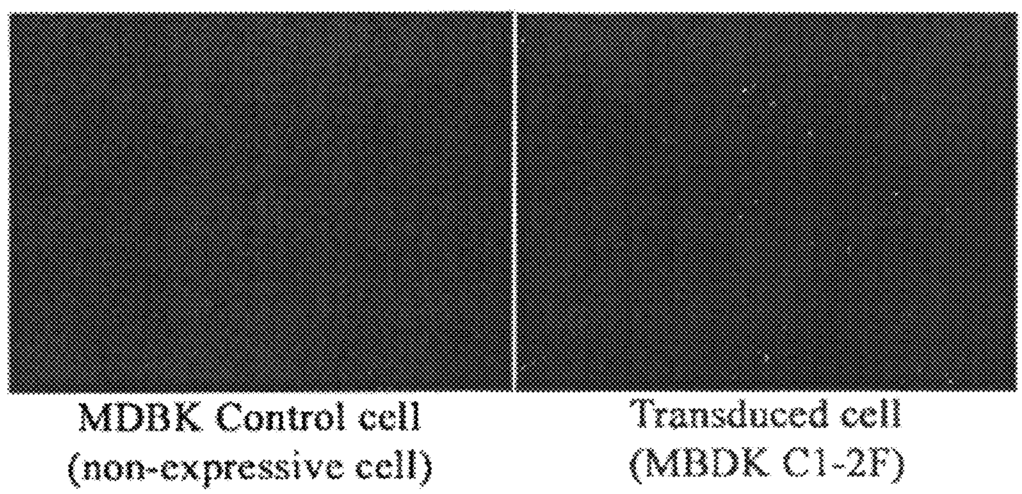
FIG. 8 shows controls and infected MDBK cells (transduced cells) at day 3 after inoculation of infectious lentivirus.

A process for production of the transduced cells may be described in detail below. Day 1 before recombinant lentiviral infection, MDBK and other mammalian cell-lines were spread on a 12-well plate for tissue culture and allowed to grow to about 60 to 70% on the inoculation day. After removing the culture supernatant, 0.5 ml of recombinant lentivirus was inoculated and 8 μg of polybrene (SIGMA H9268, Hexodimethrine bromide) per 1 ml recombinant virus was added thereto, followed by gently shaking the mixture. After incubating overnight (for 15 to 16 hours) in an incubator at 37° C. under a 5% $CO_2$ atmosphere, the medium was replaced and, on the next day, puromycin with the optimum concentration was added to the culture medium and the transduced cells were selected while continuously culturing. FIG. 8 shows representative transduced MDBK cells.

EXAMPLE 4

Detection of Prior Protein Expressed in Transduced Cell

In order to determine expression of each of bovine and elk prion proteins in the transduced cells, a fluorescent antibody (FA) assay was performed. Either the transduced cells or the normal cells were cultured then fixed using 4% paraformaldehyde (PFA) for 30 minutes and dried in order to determine whether or not prion protein was expressed on the cell's membranes. A primary antibody, 6H4 antibody (Prionics, 1:100 dilution rate) was added to the fixed cells, followed by incubation for 60 minutes. After washing the cells 3 times using PBS, anti-mouse IgG FITC conjugate (1:200 dilution rate) as a secondary antibody was added, followed by a further 60 minutes incubation. After washing the cells 6 times using PBS and placing a mounting buffer over the sample of the cells, the sample was covered with a cover slide and subjected to observation of cells using a fluorescent microscope. Compared to the MDBK control (left of FIG. 9), it was observed that the transduced cells (full length form, C1-2F) expressed prion protein (right of FIG. 9).

In order to confirm expression of prion protein using SDS-PAGE electrophoresis and western blotting, the following procedures were carried out to examine the transduced cells or normal MDBK cells. The cultured cells were washed once using PBS and, after discarding the used PBS, fresh PBS was added to the cultured cells. Then, using a scraper, cells adhered to the tissue culture flask were removed and collected in a centrifuge tube. After centrifugation at 1,200 rpm for 5 minutes to pellet the cells, the supernatant was discarded and the cells in the pellet were suspended by gently tapping the tube. After adding lysis buffer (0.5% Triton X-100, 0.5% sodium deoxycholate, 10 mM Tris-HCl [pH7.5], 150 mM NaCl, 5 mM EDTA) to the suspension, the mixture was incubated on ice for 30 minutes. After the incubation, the product was subjected to refrigerated centrifugation at 1,200 rpm for 5 minutes and the supernatant thereof was transferred into a new eppendorf tube. Using a magnetic bead (Dynabeads M-280 Sheep anti-mouse IgG), the supernatant was subjected to a semi-purification, followed by electrophoresis thereof on SDS-PAGE. The electrophoresis was conducted at 200V for 35 minutes and protein samples were transferred to a polyvinylidene difluoride (PVDF) membrane by an electrical device at 150V for 1 hour.

After the PVDF membrane was blocked using a blocking solution comprising 0.02% I-block (Tropix) dissolved in a tris-buffered saline (TBS), the membrane was incubated with the 6H4 monoclonal antibody at room temperature for 1 hour. The membrane was washed 3 times using TBST (which comprises 0.05% (v/v) Tween 20 in TBS). A goat anti-mouse IgG alkaline phosphatase-conjugated secondary antibody was diluted in 1:3,000 in TBST and incubated at room temperature for 1 hour with the membrane. Finally, the membrane was washed 3 times using TBST for 5 minutes and expression of prion protein was visualized using CDP star. Chemiluminescence signals were analyzed using the LAS 4000 (Fuji, Japan). As shown in FIG. 10, it was shown that the transduced MDBK cell exhibits relatively higher expression of PRP, compared to normal MDBK cells and other control cells expressing pLEX vector only. More particularly, referring to FIG. 10, Lane 1 is a molecular marker, Lane 2 is MDBK control cells and Lane 3 indicates MDBK C1-2F cells infected by recombinant lentivirus containing whole bovine PRNP wherein normal bovine cellular prion protein is expressed. The foregoing three kinds of cellular extracts were obtained by semi-purification using magnetic beads, and subjected to electrophoresis then western blotting (WB). Comparison of prion protein expression levels between the three types of cells is indirectly attained by comparing amounts of GAPDH, which is a normal protein contained in the cell. In other words, it can be seen from FIG. 10 that, as these cells have a substantially identical amount of GAPDH, MDBK C1-2F cells exhibit the highest expression level of prion protein.

EXAMPLE 5

Inoculation of Bovine Brain Homogenates of BSE Infected Cattle into Transduced Cell and Determination of in Vivo BSE Infection In order to determine whether PrP infection was established in the transduced cells, a bovine brain homogenates of BSE infected cattle was inoculated into the cells according to the following procedure. Firstly, the bovine brain homogenates of BSE infected cattle were diluted in a DMEM cell medium (PMA-phorbol 12-myristrate 13-acetate, fetal bovine serum, penicillin, streptomycin, non-essential amino acid contained in DMEM) to a concentration of 0.25 to 0.5%, and 100 μl of the prepared homogenates was inoculated onto a 96-well tissue culture plate containing 60 to 70% confluent cells. After incubation cells were transferred from 24-well tissue culture plates, to a 25 $cm^2$ tissue culture flask and then a 75 $cm^2$ tissue culture flask, after 4 and 6 day intervals respectively.

BSE infection was identified by ELISA (IDEXX HerdChek) performed on the cultured cells in the 75 $cm^2$ flask. For the normal MDBK cells shown in FIG. 11, when the cells inoculated with BSE infected bovine brain homogenates and the cells without inoculation were compared, the ELISA absorbance ratio was 1.07 (inoculated/non-inoculated cells=0.041/0.038). On the other hand, the transduced cells exhibited an absorbance ratio of 2.4 (inoculated/non-inoculated cells=0.047/0.113), in turn confirming the BSE infection. The transduced cells with infection were subjected to limiting dilution using a 96-well plate. Through such limiting dilution, pure cloned infected cells were obtained. In order to select infected cells among the cloned cells, SSCA (Klohn, P.

C., Stoltze, L., Flechsig, E., Enari, M. & Weissmann, C. (2003) A quantitative, highly sensitive cell-based infectivity assay for mouse scrapie prions *Proc Natl Acad Sci USA* 100, 11666-11671) was utilized. As a result, infected clones showing a strong positive response were found (shown in FIG. 12) thereby confirming that the transduced cells using recombinant lentivirus have improved susceptibility to infectious abnormal prions.

EXAMPLE 6

Determination of Persistent Infectivity of BSE Infected Cells

Figure 13:
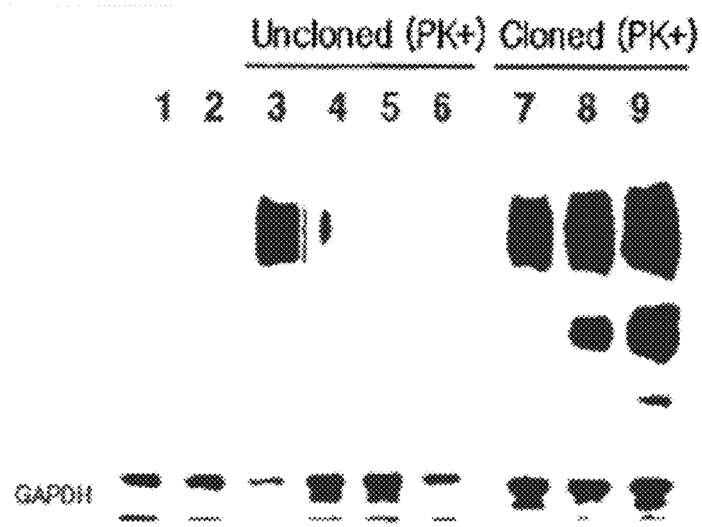
FIG. 13 illustrates results of western blotting to demonstrate continuous $PrP^{BSE}$ infection of transduced MDBK cells.

As for isolation of the transduced cell clone with BSE infection identified as described above, a cell cloning experiment was performed, by re-cloning the transduced cell clone while adjusting the number of cells in order to introduce about 0.5 cells into each well of a 96-well plate, thereby obtaining persistently infected PrP $^{BSE}$ cell-lines. As shown in FIG. 13, western blotting (WB) results demonstrated that an uncloned cell (uncloned (PK+) CELL) has undergone persistent cell subculture and the infected cell disappeared before 20 passages (subcultures). On the other hand, the cloned cell (cloned (PK+) cell) exhibited persistent infection even after 26 passages by continuous subculture. In addition, PK (that is, proteinase K) resistance as a feature of the abnormal prion protein was identified by western blotting (WB). Briefly, the control cells have no prion protein band (Lane 2 of FIG. 13) indicating the prion protein has no PK resistance, since prion protein in these cells was completely degraded by PK treatment. On the other hand, the cell persistently infected by the abnormal prion protein clearly exhibited three specific bands on the western blot indicating the prion protein has PK resistance (Lanes 3, 4, 7, 8 and 9 of FIG. 13). A cell-line having the foregoing characteristics was named M2B and deposited in the Korean Biological Resource Center (KBRC) (Accession No. KCTC 11594BP) dated Nov. 24, 2009.

EXAMPLE 7

BSE Infection in Other Cells Except for MDBK Cells

In view of the exemplary case of M2B cells according to the present invention, it was demonstrated that the transduced cells using recombinant lentivirus may be infected with PrP$^{BSE}$ which is a representative prion disease. Furthermore, for other cells such as Vero, N2a, RK-13, etc. expression of bovine cellular prion protein in these cells was performed by the same recombinant lentivirus expression system as used for MDBK. As a selection agent, puromycin was used to select the transduced cells. The selected transduced cells were incubated in a 96-well cell culture plate, followed by inoculation thereof with a 0.25% (w/v) bovine brain homogenates of BSE infected cattle. When the cells were confluent and should undergo subculture, SSCA was performed to determine whether or not BSE infection had occurred. Positive cells, found using SSCA, were subjected to continuous subculture. From the results of these experiments, it was shown that infected cells were found in all of the transduced cells infected with BSE positive cattle brain materials (FIGS. 14 to 16).

Figure 14:
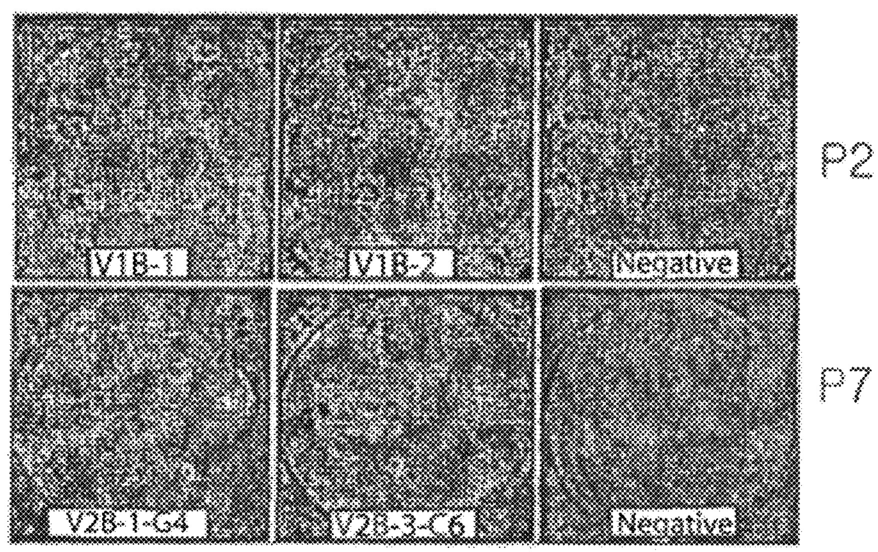
FIG. 14 illustrates SSCA results to demonstrate $PrP^{BSE}$ infection of transduced Vero cells.
Figure 15:
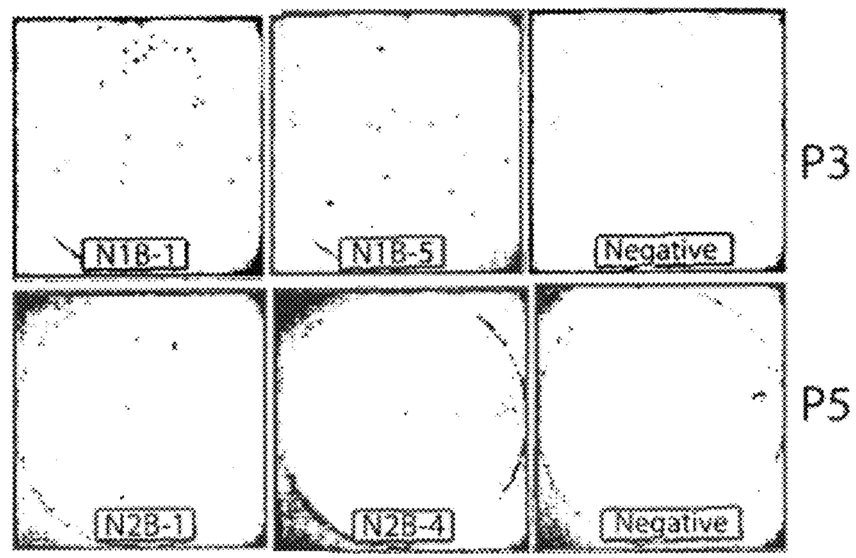
FIG. 15 illustrates SSCA results to demonstrate $PrP^{BSE}$ infection of transduced N2a cells.
Figure 16:
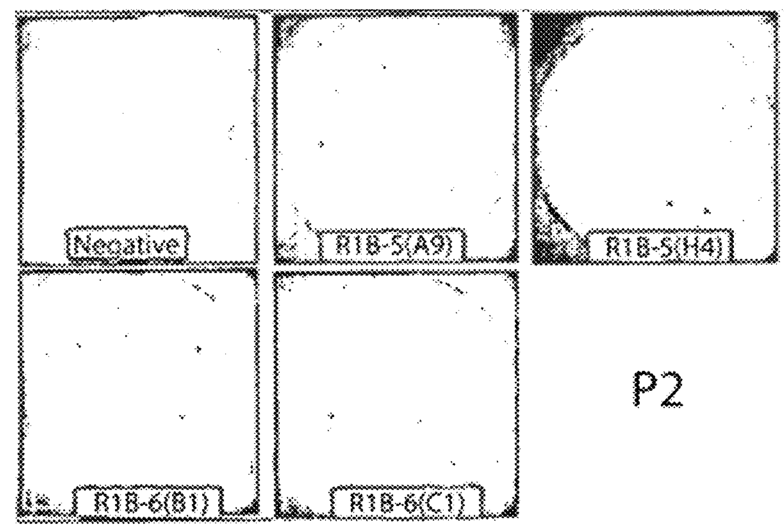
FIG. 16 illustrates SSCA results to demonstrate $PrP^{BSE}$ infection of transduced RK-13 cells.

FIG. 14 shows SSCA results of PrP$^{BSE}$ infection in transduced Vero cells, FIG. 15 shows SSCA results of PrP$^{BSE}$ infection in transduced N2a cells, and FIG. 16 shows SSCA results of PrP$^{BSE}$ infection in transduced RK-13 cells.

EXAMPLE 8

Infection of Transduced Cells Using Brain Material of CWD Infected Elk

According to the same procedure as used for preparation of BSE infected cells, the possibility of in vivo infection using abnormal prion was investigated with regard to prion diseases of other livestock animals. In particular, in order to prepare cells susceptible to an elk prion disease called chronic wasting disease (CWD), elk PRNP genes obtained from brain cells of the elk was amplified via PCR and the amplified PCR product was cloned in the pGEM-T Easy plasmid vector (FIG. 2). DNA sequencing was used to determine whether an elk gene was correctly cloned (FIG. 4). After cloning the elk PRNp into the pLEX MCS vector, the identity of the gene was confirmed again by agarose gel electrophoresis (FIG. 5). The process for production of recombinant lentivirus was substantially the same as described in Examples 2 to 4 above. Consequently, normal elk prion protein was expressed in each of RK-13, Vero and N2a cells. Transduced cells shown to have PRP expression were inoculated with 0.25% brain homogenates of CWD infected elk and, according to the same process as described in EXAMPLE 7, cell subculture was performed. Finally, SSCA and western blotting (WB) were performed to determine whether CWD infection had occurred.

Figure 17:
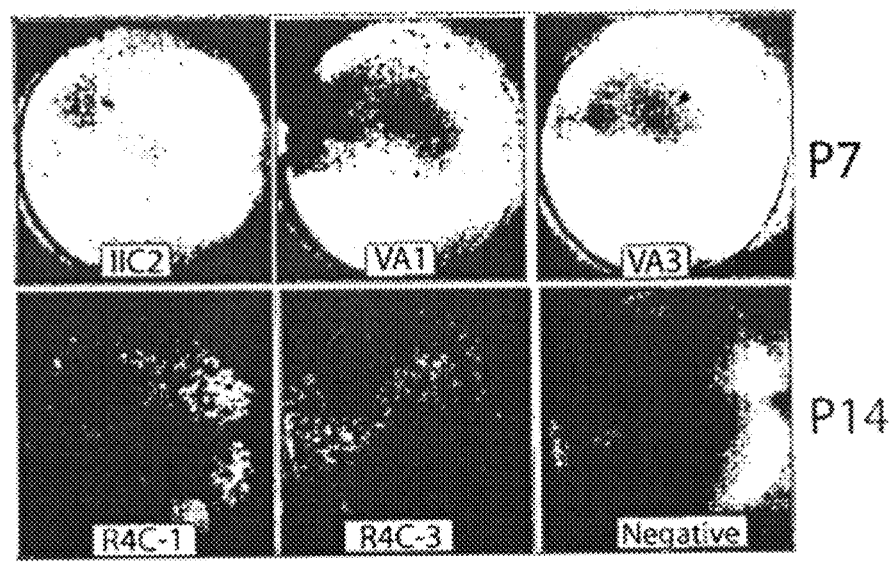
FIG. 17 illustrates SSCA results to demonstrate that transduced RK-13 cells were infected with elk abnormal prion ($PrP^{CWD}$) related to chronic wasting diseases.
Figure 18:
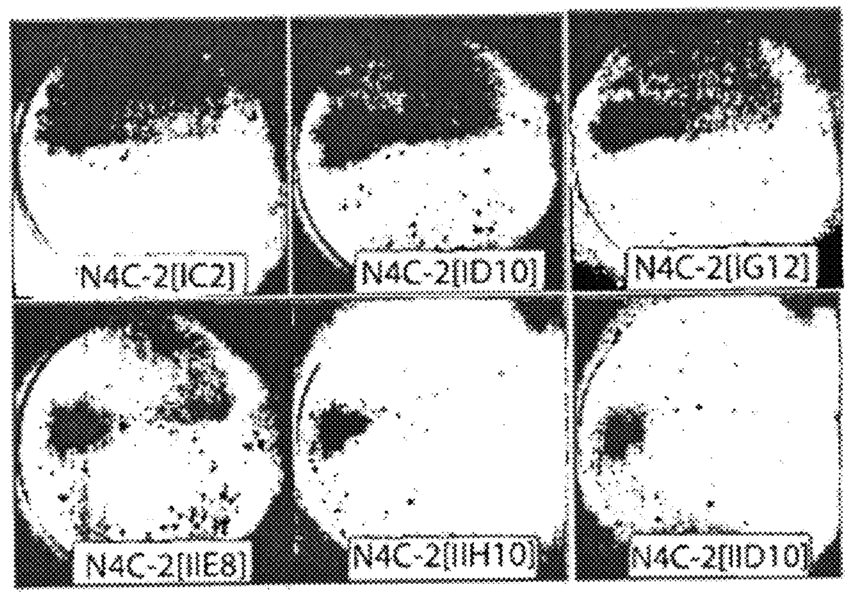
FIG. 18 illustrates SSCA results to demonstrate $PrP^{CWD}$ infection of transduced N2a cells.
Figure 19:
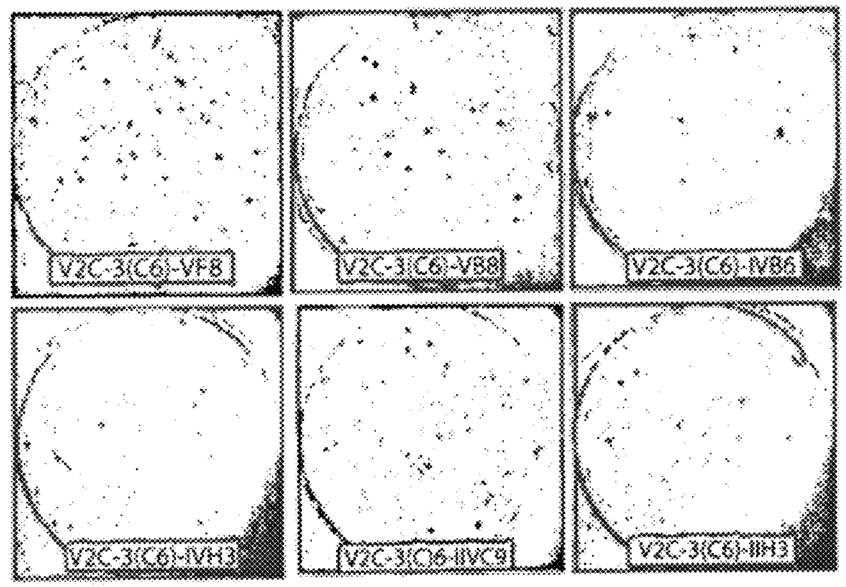
FIG. 19 illustrates SSCA results to demonstrate $PrP^{CWD}$ infection of transduced Vero cells.

FIG. 17 illustrates SSCA results to demonstrate that transduced RK-13 cells were infected with elk abnormal prion protein (PrP$^{CWD}$) related to chronic wasting diseases (CWD), FIG. 18 illustrates SSCA results to demonstrate PrP$^{CWD}$ infection of transduced N2a cells, and FIG. 19 illustrates SSCA results to demonstrate PrP$^{CWD}$ infection of transduced Vero cells. As shown in FIGS. 17 to 19, SSCA demonstrated that all of the transduced cells with CWD infection exhibited infected cells.

Figure 20:
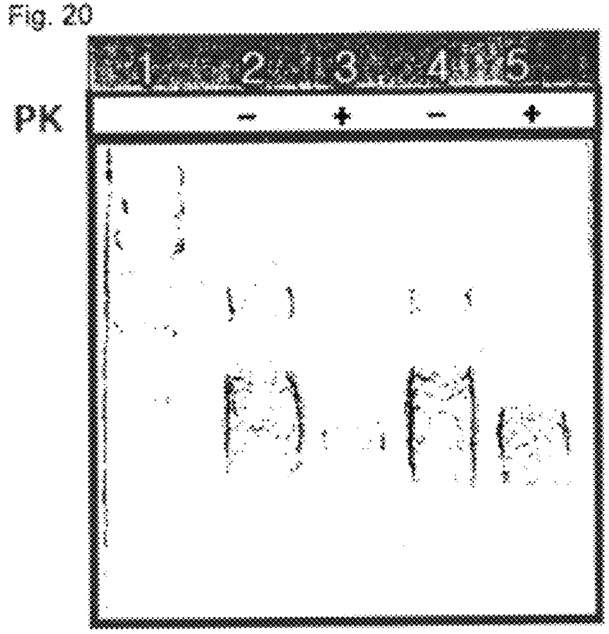
FIG. 20 illustrates western blotting results to demonstrate $PrP^{CWD}$ infection of transduced RK-13 cells.
Figure 21:
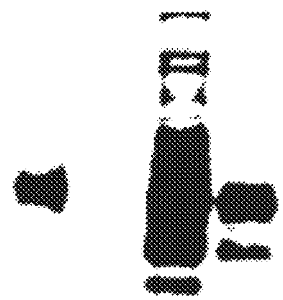
FIG. 21 illustrates western blotting results to demonstrate $PrP^{CWD}$ infection of transduced N2a cells.

CWD infection of RK-13 and N2a cells was also demonstrated by western blotting (WB) (FIGS. 20 and 21). That is, FIG. 20 shows western blotting (WB) results of PrP$^{CWD}$ infection in transduced RK-13 cells while FIG. 21 shows western blotting (WB) results of PrP$^{CWD}$ infection in transduced N2a cells.

While the present invention has been described with reference to the , it will be understood by those skilled in the related studies that various modifications and variations may be made therein without departing from the scope of the present invention as defined by the appended claims.

The invention claimed is:

1. A method for preparation of a cell persistently infected with bovine spongiform encephalopathy (BSE), comprising:

extracting a DNA comprising a normal prion protein gene from bovine brain and cloning the normal prion protein gene into a lentivirus transfer vector;

inserting the lentivirus transfer vector comprising the normal prion protein gene into a lentivirus to produce a recombinant lentivirus;

inoculating a MDBK cell line with the recombinant lentivirus to produce a transduced cell expressing a normal prion protein;

selecting one of multiple transduced cells that expresses the normal prion protein;

inoculating the selected transduced cell expressing the normal prion protein with a BSE-infected bovine brain homogenate to produce a clone capable of exhibiting infection even after 26 passages by continuous subculture.

2. The method according to claim 1, wherein the method is conducted by culturing the infected cell in a medium containing phorbol 12-myristate 13-acetate.

* * * * *

SEQUENCE LISTING

```
<160> NUMBER OF SEQ ID NOS: 4

<210> SEQ ID NO 1
<211> LENGTH: 795
<212> TYPE: DNA
<213> ORGANISM: Bos taurus coreanae
```

<400> SEQUENCE: 1

```
atggtgaaaa gccacatagg cagttggatc ctggttctct ttgtggccat gtggagtgac     60
gtgggcctct gcaagaagcg accaaaacct ggaggaggat ggaacactgg ggggagccga    120
tacccaggac agggcagtcc tggaggcaac cgttatccac ctcagggagg gggtggctgg    180
ggtcagcccc atggaggtgg ctggggccag cctcatggag gtggctgggg ccagcctcat    240
ggaggtggct ggggtcagcc ccatggtggt ggctggggac agccacatgg tggtggaggc    300
tggggtcaag gtggtaccca cggtcaatgg aacaaaccca gtaagccaaa aaccaacatg    360
aagcatgtgg caggagctgc tgcagctgga gcagtggtag gggccttggg tggctacatg    420
ctgggaagtg ccatgagcag gcctcttata cattttggca gtgactatga ggaccgttac    480
tatcgtgaaa acatgcaccg ttaccccaac caagtgtact acaggccagt ggatcagtat    540
agtaaccaga acaactttgt gcatgactgt gtcaacatca cagtcaagga acacacagtc    600
accaccacca ccaaggggga gaacttcacc gaaactgaca tcaagatgat ggagcgagtg    660
gtggagcaaa tgtgcattac ccagtaccag agagaatccc aggcttatta ccaacgaggg    720
gcaagtgtga tcctcttctc ttcccctcct gtgatcctcc tcatctcttt cctcattttt    780
ctcatagtag gatag                                                     795
```

<210> SEQ ID NO 2
<211> LENGTH: 771
<212> TYPE: DNA
<213> ORGANISM: Cervus elaphus nelsoni

<400> SEQUENCE: 2

```
atggtgaaaa gccacatagg cagctggatc ctagttctct ttgtggccat gtggagtgac     60
gtcggcctct gcaagaagcg accaaaacct ggaggaggat ggaacactgg ggggagccga    120
tacccgggac agggaagtcc tggaggcaac cgctatccac ctcagggagg gggtggctgg    180
ggtcagcccc atggaggtgg ctggggccaa cctcatggag gtggctgggg tcagccccat    240
ggtggtggct ggggacagcc acatggtggt ggaggctggg gtcaaggtgg tacccacagt    300
cagtggaaca agcccagtaa accaaaaacc aacatgaagc atgtggcagg agctgctgca    360
gctggagcag tggtaggggg cctcggtggc tacatgctgg gaagtgccat gagcaggcct    420
cttatacatt ttggcaatga ctatgaggac cgttactatc gtgaaaacat gtaccgttac    480
cccaaccaag tgtactacag gccagtggat cagtataata accagaacac ctttgtgcat    540
gactgtgtca acatcacagt caagcaacac acagtcacca ccaccaccaa gggggagaac    600
ttcaccgaaa ctgacatcaa gatgatggag cgagttgtgg agcaaatgtg catcacccag    660
taccagagag aatccgaggc ttattaccaa agaggggcaa gtgtgatcct cttctcctcc    720
cctcctgtga tcctcctcat ctctttcctc atttttctca tagtaggata g             771
```

<210> SEQ ID NO 3
<211> LENGTH: 35
<212> TYPE: DNA
<213> ORGANISM: Artificial Sequence
<220> FEATURE:
<223> OTHER INFORMATION: Artificial primer
<220> FEATURE:
<221> NAME/KEY: gene
<222> LOCATION: (1)..(35)
<223> OTHER INFORMATION: forward primer

<400> SEQUENCE: 3

-continued

```
agcggccgcg ccaccatggt gaaaagccac atagg                              35


<210> SEQ ID NO 4
<211> LENGTH: 32
<212> TYPE: DNA
<213> ORGANISM: Artificial Sequence
<220> FEATURE:
<223> OTHER INFORMATION: Artificial primer
<220> FEATURE:
<221> NAME/KEY: gene
<222> LOCATION: (1)..(32)
<223> OTHER INFORMATION: reverse primer

<400> SEQUENCE: 4

cggctcgagc tatcctacta tgagaaaaat ga                                 32
```